(12) United States Patent
Koll et al.

(10) Patent No.: US 11,028,565 B2
(45) Date of Patent: *Jun. 8, 2021

(54) FLUID TREATMENT AND DISPOSAL SYSTEM AND METHODS OF USE

(71) Applicant: Safe Health Solutions, LLC, Omaha, NE (US)

(72) Inventors: Gregory Scott Koll, Omaha, NE (US); James R. Stark, Omaha, NE (US); Thomas S. Hicks, Omaha, NE (US); Lorie Margaret Koll, Omaha, NE (US)

(73) Assignee: SAFE HEALTH SOLUTIONS, LLC, Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/214,903

(22) Filed: Dec. 10, 2018

(65) Prior Publication Data

US 2019/0345701 A1    Nov. 14, 2019

Related U.S. Application Data

(63) Continuation of application No. 15/584,364, filed on May 2, 2017, now Pat. No. 10,151,084.

(Continued)

(51) Int. Cl.
| | |
|---|---|
| *E03C 1/12* | (2006.01) |
| *A61L 2/10* | (2006.01) |
| *E03C 1/18* | (2006.01) |
| *E03C 1/126* | (2006.01) |
| *A61L 9/20* | (2006.01) |
| *E03C 1/181* | (2019.01) |
| *E03C 1/186* | (2019.01) |
| *E03C 1/182* | (2006.01) |

(Continued)

(52) U.S. Cl.
CPC ............... *E03C 1/126* (2013.01); *A61L 2/10* (2013.01); *A61L 9/20* (2013.01); *E03C 1/181* (2013.01); *E03C 1/182* (2013.01); *E03C 1/186* (2013.01); *E03C 1/22* (2013.01); *E03F 5/0407* (2013.01)

(58) Field of Classification Search
CPC .......... E03C 1/266; E03C 1/126; E03C 1/128; E03C 1/29; A47K 10/48; A61L 2/10
See application file for complete search history.

(56) References Cited

U.S. PATENT DOCUMENTS

| | | | |
|---|---|---|---|
| 6,666,966 B1 * | 12/2003 | Schluttig | ................. E03C 1/126 210/163 |
| 7,900,288 B2 * | 3/2011 | Fima | ....................... C02F 1/325 4/287 |

(Continued)

*Primary Examiner* — Janie M Loeppke
(74) *Attorney, Agent, or Firm* — Perkins Coie LLP (57) ABSTRACT

A fluid treatment and disposal system includes a sink, having a basin, a sink drain inlet, and a sink drain trap. An open cavity is disposed behind a rearward wall of the sink basin, between a top portion of the sink and the sink drain trap. A curved transition surface receives fluid entering the sink. Embodiments of the drain are shaped to promote the evacuation of fluid from the basin while limiting turbulence. An exhaust port fluidly coupled with the open cavity evacuates the open cavity and surrounding environment. Embodiments optionally associate one or more of the following with the open cavity: Ultra-Violet (UV) Germicidal Lights, and Ozone water, copper-silver ionization, and/or sanitizing agent injection systems.

19 Claims, 9 Drawing Sheets

Related U.S. Application Data

(60) Provisional application No. 62/330,649, filed on May 2, 2016.

(51) Int. Cl.
*E03C 1/22* (2006.01)
*E03F 5/04* (2006.01)

(56) References Cited

U.S. PATENT DOCUMENTS

| | | | |
|---|---|---|---|
| 9,994,462 B2 * | 6/2018 | Zereshkian | C02F 1/008 |
| 10,151,084 B2 * | 12/2018 | Koll | A61L 9/20 |
| 2008/0213128 A1 * | 9/2008 | Rudy | A61L 2/10 |
| | | | 422/24 |
| 2009/0211019 A1 * | 8/2009 | Schluttig | E03C 1/04 |
| | | | 4/584 |
| 2012/0298882 A1 * | 11/2012 | Vitali | E03C 1/126 |
| | | | 250/436 |
| 2015/0376881 A1 * | 12/2015 | Moe | A47K 10/48 |
| | | | 4/638 |
| 2016/0281346 A1 * | 9/2016 | Clear | A47K 3/405 |

* cited by examiner

FLUID TREATMENT AND DISPOSAL SYSTEM AND METHODS OF USE

CROSS-REFERENCE TO RELATED APPLICATIONS

The present application is continuation of U.S. application Ser. No. 15/584,364, titled "Fluid Treatment and Disposal System and Methods of Use", filed May 2, 2017, which claims the benefit priority of U.S. Provisional Patent Application Ser. No. 62/330,649, titled "Fluid Treatment and Disposal System and Methods of Use", filed May 2, 2016, both of which are incorporated herein in their entirety.

BACKGROUND

Various types of sinks, lavatories, wash areas, and fluid disposal areas are used in hospitals, pharmaceutical manufacturing facilities, pharmacies, and laboratories, where bacteria and viruses are plentiful. The sink and wash areas provide staff and other individuals with a location to wash their hands and various types of equipment. Such areas also provide a location where various liquids, which may be contaminated with bacteria or viruses, are disposed. However, as the hands and equipment are washed in the sink, bacteria and viruses are transferred from the hands and equipment into the water, which flows into the sink. The contaminated water splashes into the sink basin, swirls around the basin, and flows into a drain. This turbulent fluid activity can aerosolize bacteria, viruses, and other biological contaminants from the water.

Inside the drain, the contaminated liquids sit within a drain trap. As it sits in the trap, the viruses and bacteria are allowed to multiply within the plumbing, regardless of how well the sink basin is cleaned. Gasses that occasionally bubble through the sink drain trap carry the bacteria and viruses up from the plumbing and into the basin or otherwise become airborne. Moreover, fluids that drain from the sink, into the trap, agitate the contaminated fluid and further aerosolize the biological contaminants.

The airborne biological contaminants pose health risks to those in a significant area surrounding the sink. Oftentimes, individuals surrounding the sink in hospitals are immuno-compromised, making them more likely to become ill as a result of the airborne contaminants. Similarly, pharmaceutical products in pharmaceutical manufacturing facilities and pharmacies can be easily contaminated by the airborne biological contaminants, requiring the disposal of the pharmaceutical products. Such product losses cause significant financial loss annually.

SUMMARY

This Summary is provided to introduce a selection of concepts in a simplified form that are further described below in the Detailed Description. This Summary, and the foregoing Background, is not intended to identify key aspects or essential aspects of the claimed subject matter. Moreover, this Summary is not intended for use as an aid in determining the scope of the claimed subject matter.

The present disclosure provides embodiments of a fluid treatment and disposal system. Various embodiments of the technology are provided as a sink, having a basin with a bottom portion, a forward wall portion, rearward wall portion, and opposite sidewall portions. A drain is positioned at a lower end of the basin, such as within the rearward wall portion. In some embodiments, the drain includes a drain plate having a plurality of openings that penetrate the plate member in an orientation that allows an even distribution of fluid to flow through the drain. Various embodiments of the sink include a faucet that controls a flow of fluid from one or more fluid sources. Embodiments of the basin shape the forward wall portion to extend from an upper vertical portion toward a lower transition portion, adjacent the drain, to receive a fluid stream from the faucet in a gradual fashion that reduces or eliminates turbulent splashing and gently directs the fluid toward the drain.

In various embodiments, an open cavity is disposed behind the rearward wall portion of the basin and extends between a top portion of the sink and a drain trap. An exhaust port is placed in fluid communication with the open cavity and a central exhaust system or a dedicated exhaust system. The exhaust port places the open cavity under a negative pressure and evacuates the gaseous headspace of the open cavity away from the sink. In some embodiments, the gaseous exhaust may be directed to a system for treating one or more types of contaminated or volatile gases. The open cavity is, in some embodiments, maintained at a negative pressure in relation to the area in which the sink is located in order to draw air from outside the sink. This helps to capture, entrain, and evacuate as many aerosolized biological contaminants, bacteria, or viruses as possible from the sink area.

In some embodiments, one or more germicidal ultra-violet lights are disposed within the open cavity. The UV light exposure kills bacteria, parasites, fungi, viruses, molds and other biological contaminants that may be growing in the fluids within the open cavity and the drain trap. In particular embodiments, elongated germicidal ultra-violet lights are positioned within an upper area of the open cavity, adjacent a top portion of the sink, so that their light is directed throughout the entire open cavity and into the drain trap while staying substantially out of contact with any liquid flowing through the open cavity.

Embodiments of the present technology use one or more sanitizing agent injectors and/or spray bars at various locations throughout the open cavity and/or into the exhaust port to help clean the surfaces of the open cavity and the exhaust port. The sanitizing agent injectors and spray bars may inject one or more of: ozone water (or other ozone solution); copper-silver ionization solution (such as domestic cold water treated with a copper/silver ionization generation unit); or similar sanitizing agent. The ozone water, copper-silver ionization solution, and/or sanitizing agent may be injected into the open cavity continuously or intermittently, whether the sink is in use or not.

In various embodiments of the present technology, control systems provide monitoring and control to ensure that the features of the sink are functioning according to their intended design. In one embodiment, sensors within the open cavity and/or the exhaust port monitor pressure and/or airflow. The control system receives and monitors data from the sensors and can initiate, terminate, and vary the exhaust through the exhaust port according to the data received from the sensors. In another embodiment, sensors are positioned within the open cavity and/or the drain trap that monitor UV light and/or an amount of ozone water (or other ozone solution), copper-silver ionization solution, or similar sanitizing agent. The control system may direct the injections to occur on a timed interval, at any time that the faucet is turned on or off, or according to data from the sensors that are not in line with desired or predetermined operational parameters. The data received from the sensors may be recorded by the control system and reported to a user in real-time or stored for delivery or retrieval at a later time. The control system may be provided to receive remote or locally provided inputs from a user that initiates, terminates, and varies the operation of exhaust port, germicidal ultra-violet lights, and the sanitizing agent injectors. The control system may also receive remote or locally provided inputs from a user that varies the operational parameters or programs of the systems associated with the sink. The control systems may be provided to provide a notification either locally (audible or visual) or electronically via e-mail, phone, or text message to initiate service and notify individuals to not use the sink when the control systems determines that any of the exhaust port, germicidal ultra-violet lights, and the sanitizing agent injectors are not functioning properly.

These and other aspects of the present system and method will be apparent after consideration of the Detailed Description and Figures herein. It is to be understood, however, that the scope of the invention shall be determined by the claims as issued and not by whether given subject matter addresses any or all issues noted in the Background or includes any features or aspects recited in this Summary.

DRAWINGS

Non-limiting and non-exhaustive embodiments of the present invention, including the preferred embodiment, are described with reference to the following figures, wherein like reference numerals refer to like parts throughout the various views unless otherwise specified.

DETAILED DESCRIPTION

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense.

With reference to FIGS. 1A-4, embodiments of the present technology reduce the transmission of biological contaminants, intended to be washed down a drain, into a surrounding environment. While the term "sink" is used herein, those of skill in the art will appreciate that the term, as it relates to the present technology, includes lavatories, wash areas, and other fluid disposal areas. Aspects of the present technology provide for the containment and destruction of infectious agents such as viruses, bacteria, protest, fungi, slime molds, algae, prions, organic infectious disease agents, or other infectious organic matter.

With reference to FIGS. 1A-3D, embodiments of the present technology are provided in the form of a sink 10, having a basin 12 with a bottom portion 14, a forward wall portion 16, rearward wall portion 18, and opposite sidewall portions 20 and 22. It is contemplated that, in certain embodiments, the sink 10 may be formed from one or more continuous walls without corners or edge portions that clearly define a bottom, a forward wall, rearward wall, and sidewalls. In some embodiments, the sink 10 includes a combination of clearly defined and continuous walls. A drain 24 may be positioned in one or more positions within the basin 12. In one embodiment, the drain 24 is placed at least partially into the rearward wall portion 18 of the basin 12. The drain 24 may extend completely or substantially across a width of the basin 12. In other embodiments, the drain 12 includes a width and height that maximizes fluid flow through the drain 24 without promoting turbulence. In particular embodiments, the drain 24 is shaped to promote the evacuation of water from the basin 12 without interrupting the flow of water or causing turbulence downstream from the drain 24. In some embodiments, the drain 24 includes a drain plate 26, having a plurality of spaced-apart, horizontally disposed bar members 28. In an exemplary, non-limiting embodiment, the drain includes ⅛ inch diameter bar members 28, spaced from one another by ⅛ inch spaces. In some embodiments, the bar members 28 may be flat while, in other embodiments, the bar members may be curvilinear or have a partially curvilinear shape. In these manners, the drain 24 is shaped to reduce fluid turbulence by allowing an even distribution of fluid to flow through the drain 24. In other embodiments, the drain plate 26 is provided in the form of a generally planar plate member having a plurality of openings that penetrate the plate member in an orientation that allows an even distribution of fluid to flow through the drain 24.

Various embodiments of the sink 10 include a faucet 30. The term "faucet," as it is used herein, will simply mean a device by which a flow of fluid (including liquid or gas) from a fluid source can be controlled. The fluid source may be a municipal water supply, a tank or other container of treated water, or a container of a particular fluid or gas chosen for specific uses of the sink 10. It is contemplated that the faucet 30 may be coupled to the sink 30 at various locations. In some embodiments, the faucet 30 extends from the sink adjacent the rearward wall portion 18; while, in other embodiments, the faucet 30 extends from one of the opposite sidewall portions 20 or 22. It is also contemplated that, in some embodiments, two or more faucets 30 may be associated with the sink 10 and coupled with one or more fluid sources. The faucets 30 may be configured according to the intended use of the sink 10, including a typical rigid neck that may be fixed in position with respect to the basin 12 or pivotable to move an outlet with respect to the basin 12. In other embodiments, the faucet 30 may include a flexible hose coupled with a nozzle output.

Embodiments of the basin 12 include a forward wall portion 16 that is shaped to extend from an upper portion 32 toward a lower transition portion 34, adjacent the drain 24. In an exemplary, non-limiting embodiment, the upper portion 32 has a depth of approximately 5.5 inches and transitions from a vertical, or nearly vertical wall, through a 4" concave radius curve, into a lower sloped portion. In such exemplary embodiments, the lower transition portion 34 is defined by a first vertical portion that transitions at a 1 inch convex radius from the lower sloped portion of the upper portion 32. In some embodiments, the vertical portion is sloped at a two degree angle from vertical, toward a front portion of the sink 10. The vertical portion of the lower transition portion 34 transitions through a 4" concave radius curve, into a lower sloped portion that passes beneath the drain 24. The lower sloped portion terminates at a 3 inch convex radius transition toward the drain trap 38. In the exemplary embodiment, the lower transition has a depth of approximately 3.5 inches, as measured at the drain 24. This provides the exemplary sink with a total basin depth of approximately nine inches. In various embodiments, the lower transition portion 34 is positioned beneath an output of the faucet 30. In this manner, portions of the first vertical portion and the curve of the transition into the lower sloped portion receives the fluid stream from the faucet 30 in a gradual fashion that reduces or eliminates turbulent splashing and gently directs the fluid toward the drain 24. In particular embodiments, the shape of the lower transition portion 34 is mated with a faucet 30 having a particular geometry and mounting location with respect to the lower transition portion 34 in order to facilitate the elimination or reduction of fluid turbulence. In particular embodiments, the basin 12 may include an overflow orifice 17 that penetrates the basin 12 and is placed in fluid communication with a drainage system. In an exemplary embodiment, depicted in FIGS. 1A and 1B, the overflow orifice 17 penetrates the forward wall portion 16.

In various embodiments, an open cavity 36 is disposed behind the rearward wall portion 18 of the basin 12 and extends between a top portion of the sink 10 and a drain trap 38. In the exemplary, non-limiting, embodiment depicted in FIG. 1A, the open cavity 36 is approximately 5.5 inches deep, 9 inches tall, and 48 inches wide. It is contemplated that some embodiments of the sink 10 may use a drain exit of various drain configurations that is associated with one or more fluid evacuation systems. For purposes of the present matter, however, such drain exits may be considered synonymous to the drain trap 38 for various functions of the sink 10. With reference to the exemplary, non-limiting embodiment depicted in FIGS. 3A-3D, the bottom portion 48 of the open cavity 36 is trough-shaped, defined by a concave radius that limits turbulent flow of the fluid as it reaches the bottom of the open cavity 36. In particular embodiments, the bottom portion is sloped from horizontal, toward the drain trap 38 in order to improve fluid flow toward the drain trap 38 and limit pooling of fluid on the bottom portion 48 when the flow of fluid into the open cavity 36 is stopped. With further reference to the exemplary embodiment depicted in FIG. 3B, a terminal, lower edge of the lower transition portion 34 of the lower wall portion 16 may be positioned in a vertical, spaced-apart relationship with the bottom portion 48, defining one end of an air gap 50. In some embodiments, the air gap 50 is defined by a forward wall portion 52 of the bottom portion 48 that extends beneath a length of the lower transition portion 34 and ends at a free distal end. An air channel 54 extends between the lower transition portion 34 and the forward wall portion 52 and fluidly couples the open cavity 36 and the environment in front of the sink 10.

In various embodiments, an exhaust port 40 is placed in fluid communication with the open cavity 36. In the exemplary embodiment, depicted in FIG. 1A, the exhaust port may be provided as a 3 inch or 4 inch diameter line, disposed at a 45° angle, upward from horizontal. In other embodiments, such as depicted in FIGS. 3A-3D, the exhaust port exits the sink 10, in a horizontal manner. The exhaust port 40 is also placed in fluid communication with an exhaust system, such as a central exhaust system or a dedicated exhaust system of various known designs (not depicted), that places a positive draft on the exhaust port 40 and the open cavity 36 under a negative pressure. In this manner, the exhaust port 40 may be used to evacuate the gaseous headspace of the open cavity 36 away from the sink 10. In various embodiments, a constant volume or variable speed fan may be associated with the exhaust port 40. In some embodiments, the gaseous exhaust may be directed to a system for treating one or more types of contaminated or volatile gases. In particular embodiments, a HEPA filter exhaust fan will be fluidly coupled with the exhaust port 40 to exhaust the air from the sink 10, treat it, and allow it to be released back into the environment around the sink 10. This allows for a less costly installation by not requiring a fully designed exhaust system that discharges to the exterior of the building. In other embodiments, the exhaust system may simply be a central exhaust system associated with a building in which the sink 10 will be used. The rate of exhaust, in some embodiments, may be designed to minimize noise by keeping the level below a Noise Criteria (NC) level of 40 that corresponds to the NC to decibel noise curves as recognized by the heating/ventilation/air conditioning industry.

Figure 1A:
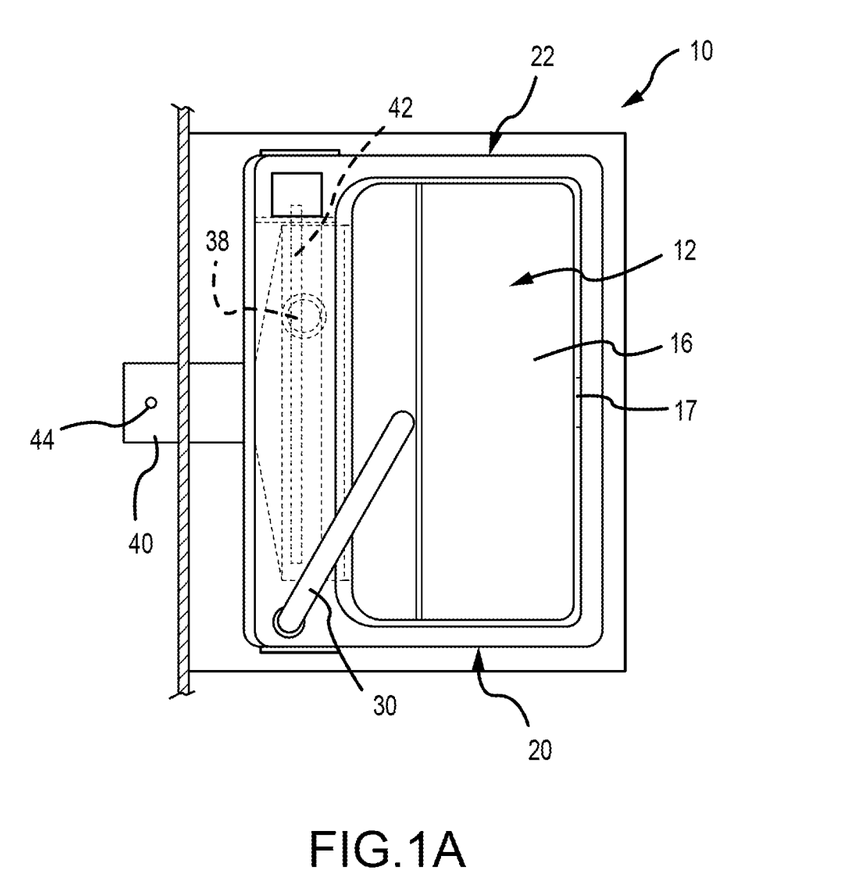
FIG. 1A depicts a top, plan view of one embodiment of a sink according to the present technology.
Figure 1B:
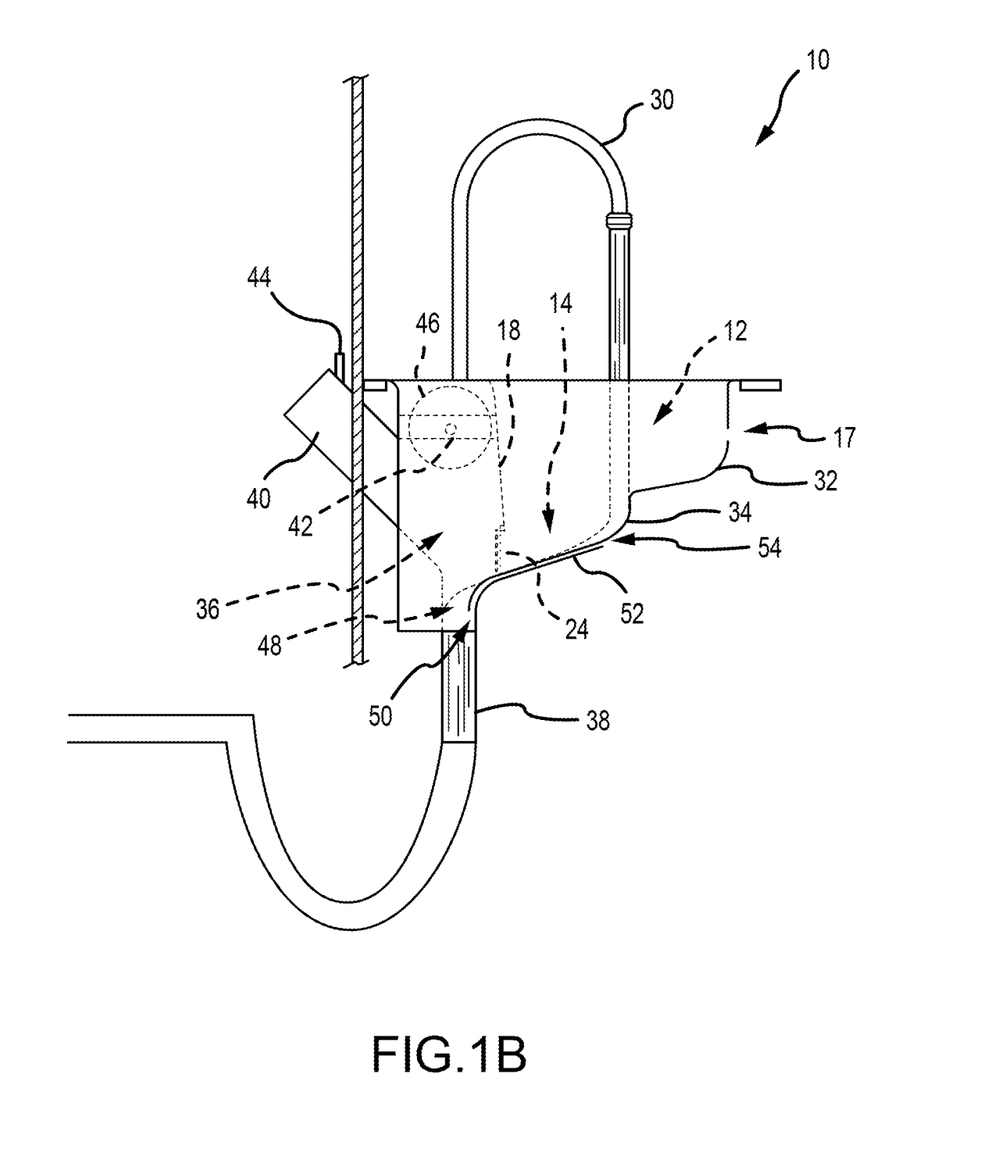
FIG. 1B depicts a side elevation view of the sink of FIG. 1A.
Figure 2A:
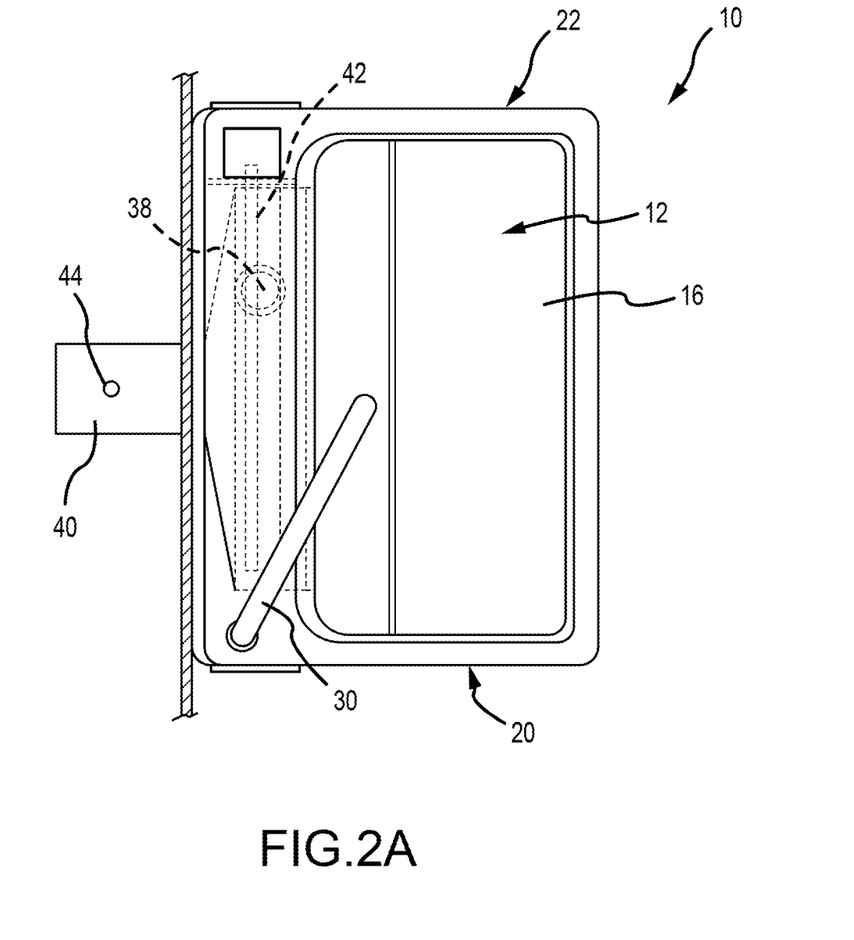
FIG. 2A depicts a top, plan view of another embodiment of a sink according to the present technology.
Figure 2B:
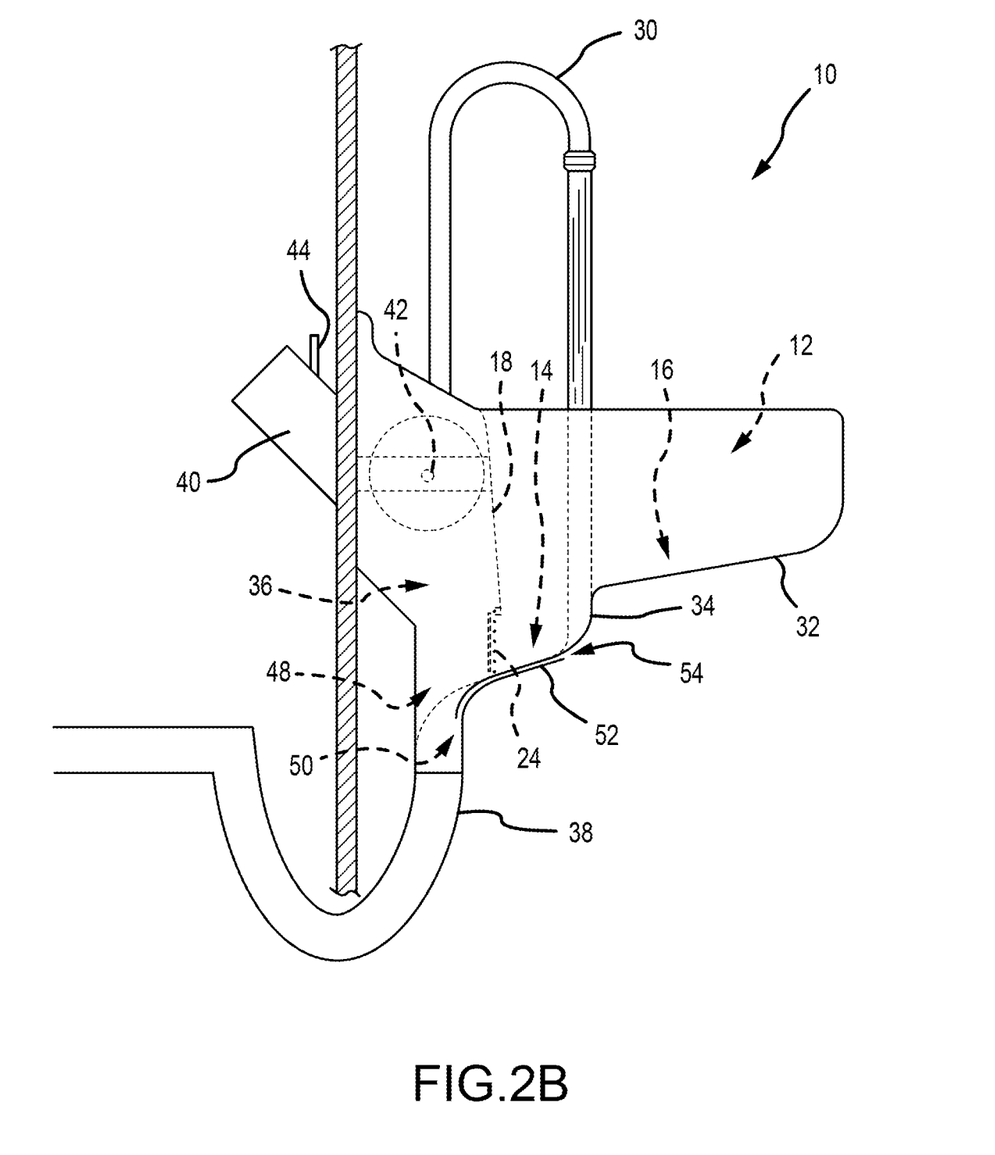
FIG. 2B depicts a side elevation view of the sink of FIG. 2A.
Figure 3A:
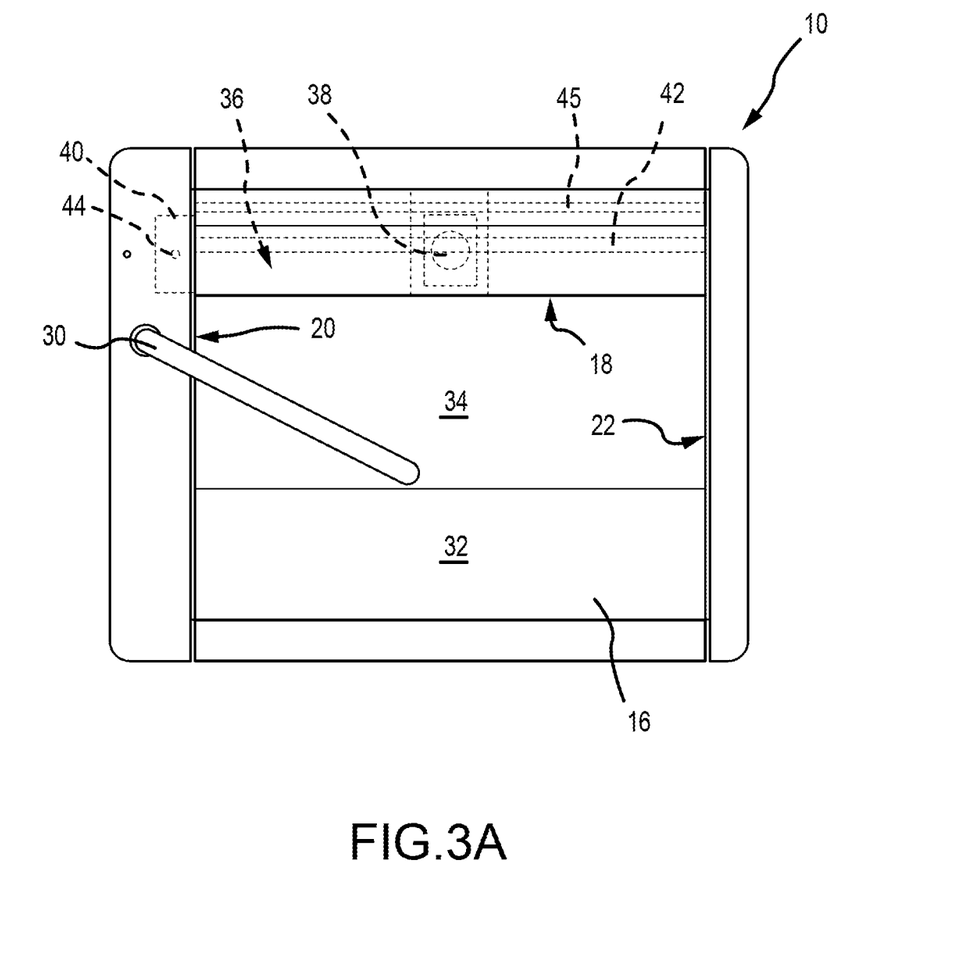
FIG. 3A depicts a top, plan view of yet another embodiment of a sink according to the present technology.
Figure 3B:
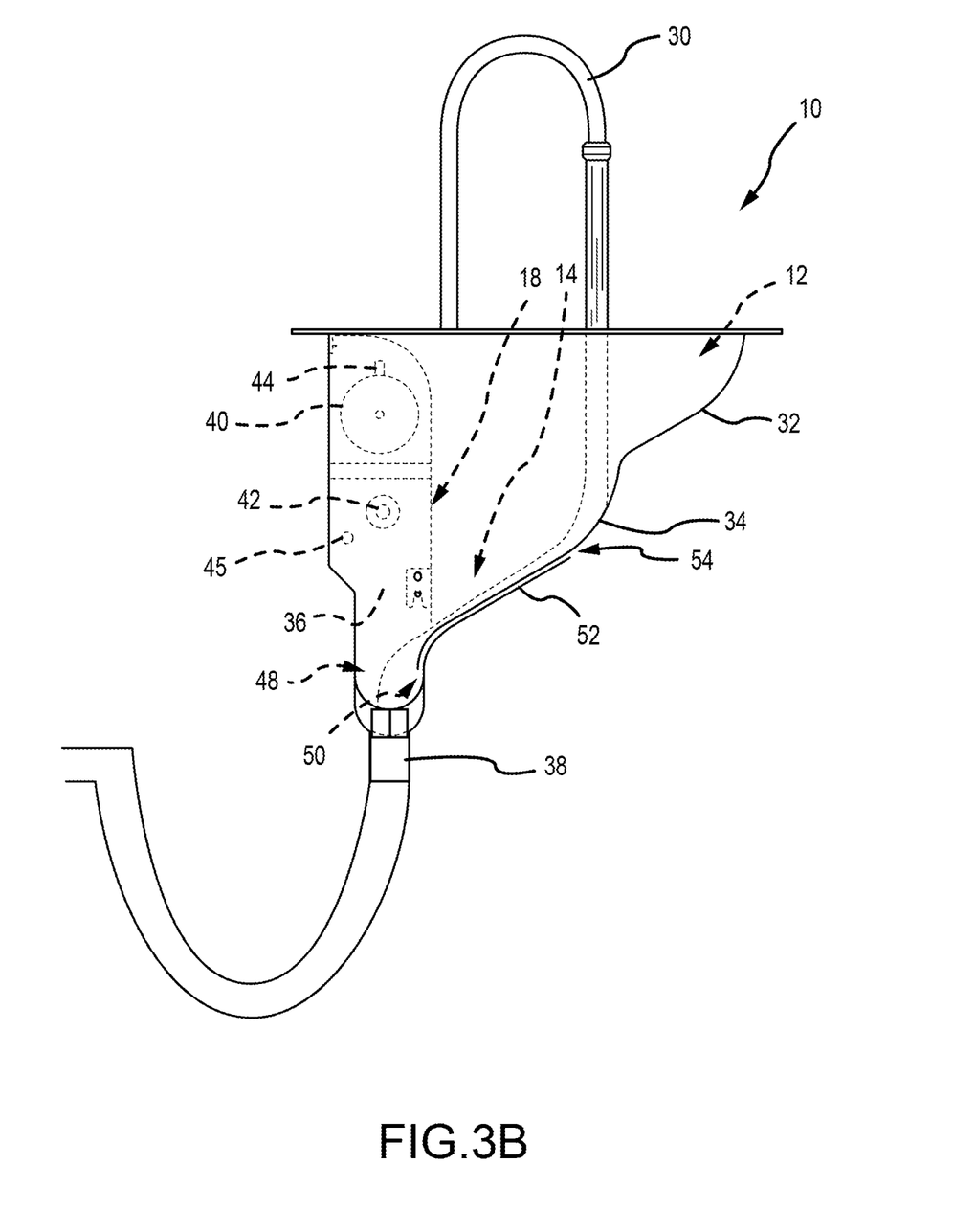
FIG. 3B depicts a side elevation view of the sink of FIG. 3A.
Figure 3C:
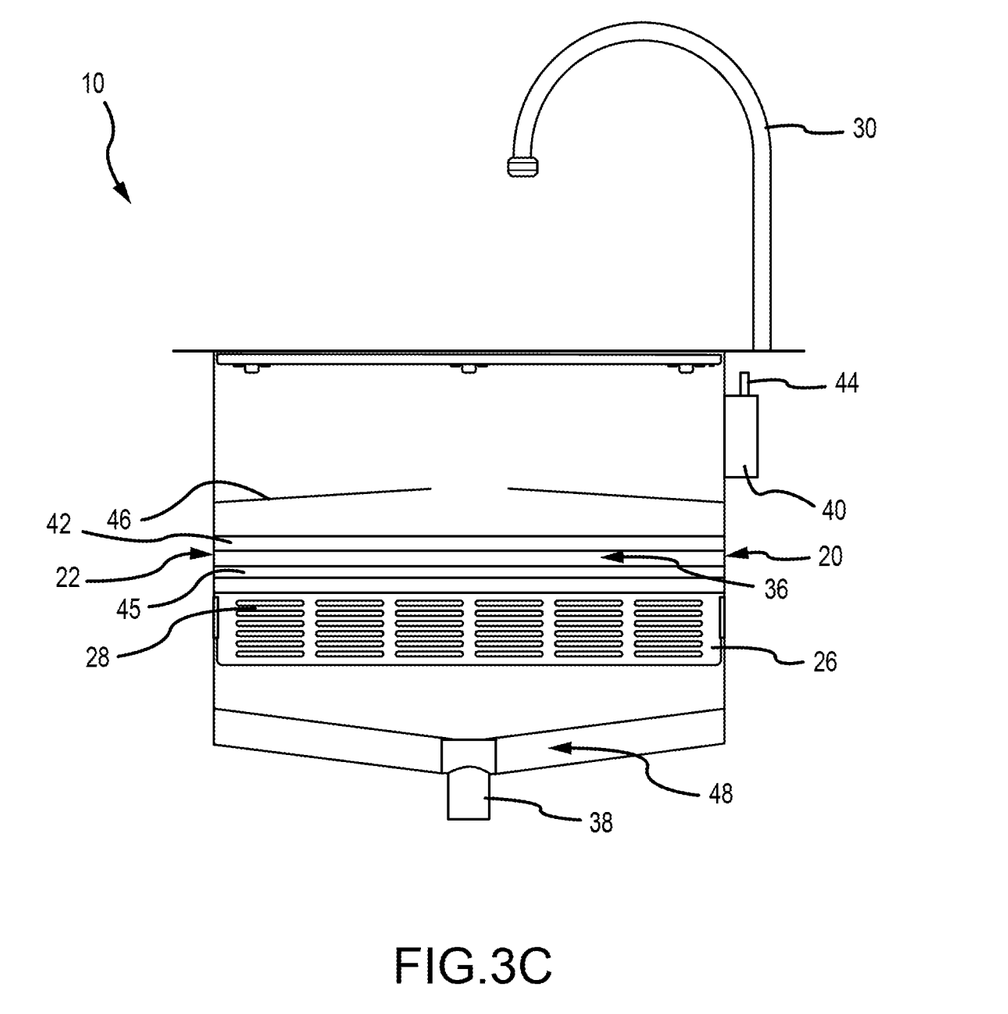
FIG. 3C depicts a rear elevation view of the sink of FIG. 3A.
Figure 3D:
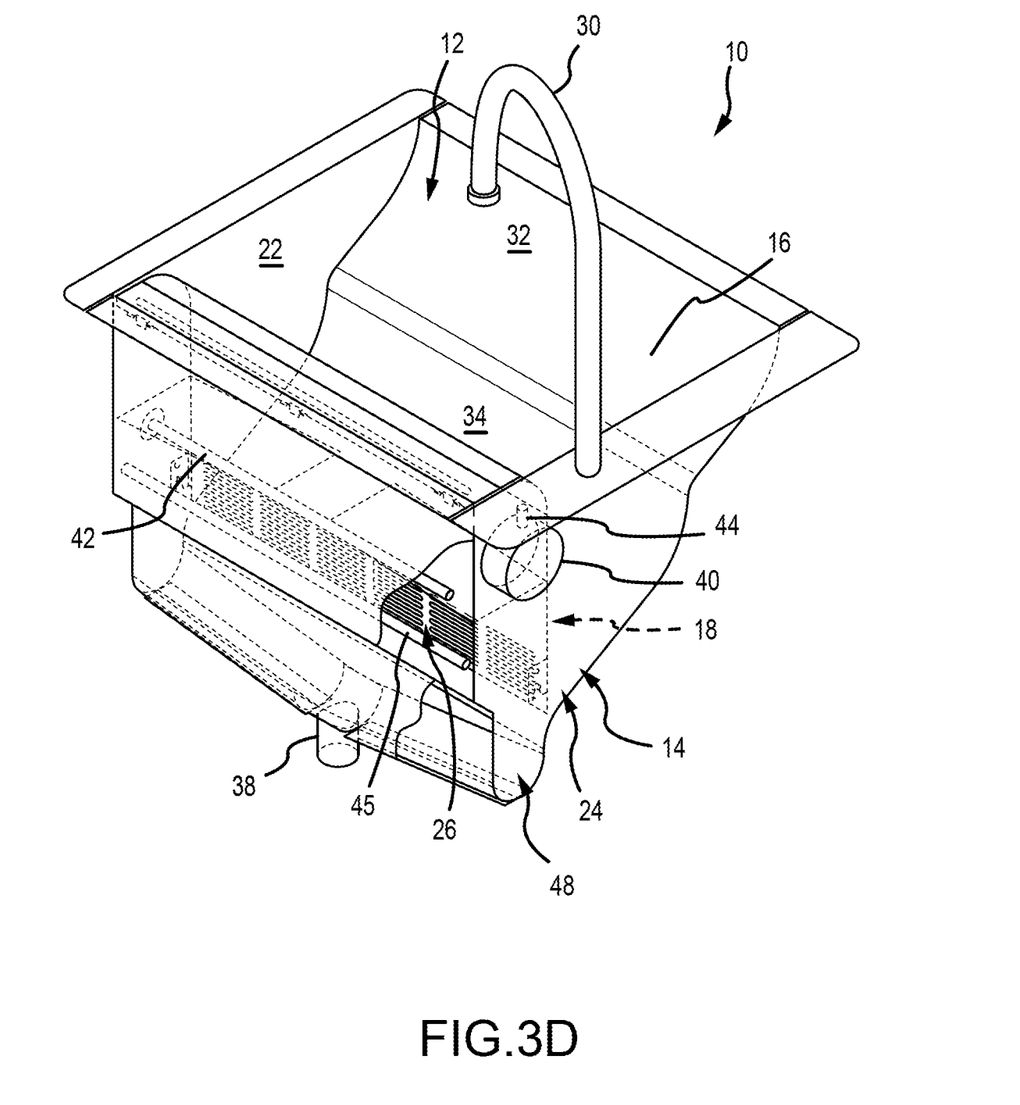
FIG. 3D depicts a rear, perspective view of the sink of FIG. 3A.

The open cavity 36 is, in certain embodiments, maintained at a negative pressure in relation to the area in which the sink 10 is located. In some aspects of the technology, air surrounding the sink 10 is drawn into the basin 12, through the drain 24, and into the open cavity 36, thus, exhausting the air surrounding the sink 10 through the exhaust port 40. Where an air channel 54 is provided, such as depicted in FIG. 3B, ambient air in front of the sink 10 will be drawn through the air channel 54 and exhausted through the exhaust port 40. This will help to evacuate as many biological contaminants, bacteria, or viruses as possible from the sink area that are aerosolized by: a) the splatter/splashing of fluids that are drained into the sink 10; b) an individual coughing, vomiting, or washing his or her hands; c) fluids that are not drained away from the sink; and/or d) the reverse flow of fluid into the drain trap 38. In this manner, the open cavity 36 becomes a biological contaminant barrier between the room in which the sink 10 is located and the drainage sewer system. When the open cavity 36 is maintained at a negative pressure, the air is continuously pulled through the drain 24 such that, when water is discharged from the faucet 30 or other fluids are poured into the basin 12, the air is pulled across the top surface of the fluid, pulling aerosols that contain biological or other contaminants into the open cavity 36 and into the exhaust system where it can be treated and/or safely exhausted.

In some embodiments, the drain 24, open cavity 36, and exhaust port are shaped and oriented with respect to one another to allow an even distribution of air to flow through the drain 24 at a velocity of between 100 feet per minute (FPM) to 4000 FPM. Airflows are determined to either obtain a capture velocity above 100 FPM at the from the drain 24 into the open cavity 36 or 100 FPM at the top plane of the basin 12, depending on the use of the sink 10. In a particular embodiment, the airflow velocity is between 100 to 500 FPM from the drain 24 into the open cavity 36 when the sink 10 is not being used for the input or disposal of fluids. Testing has shown that airflow below 450 FPM will not produce noise levels that tend to disturb individuals near the sink 10. The testing has further shown that airflow volumes that create an air velocity of between 100 to 2500

FPM from the rain 24 into the open cavity 36 provides acceptable capture velocities for smells and undesirable particulate within the air. Furthermore, the testing has also shown that airflow volumes that create an air velocity of between 100 to 2500 FPM from the drain 24 into the open cavity 36 provides acceptable capture velocities for gaseous or toxic fumes from ozone-water and sanitizing agents injected into the rearward cavity from escaping into the basin 12 or the room in which the sink 10 is located. Velocity levels above 2000 FPM from the drain 24 into the open cavity 36 produce capture velocities for heavier particulates that are entrained within the air. Accordingly, particular embodiments of the present technology use an airflow range of between 20 cubic feet per minute (CFM) to 50 (CFM) when the sink 10 is not in use and 50 to 500 CFM or greater when the sink 10 is in use. In some embodiments, the exhaust may operate at a constant volume whether the sink 10 is in use or not. The sink 10 may implement an airflow meter or other known device to monitor and measure the volume of the exhaust. In particular embodiments, the exhaust system may implement a fan or motorized damper to be fluidly coupled to the exhaust port 40. One or more device controls may be provided to vary the exhaust airflow from a lower volume rate when the sink is not in use and a higher volume rate when the sink is in use.

One or more aspects of the present technology treat the liquid and gaseous fluids as they pass through the drain 24 and the open cavity 36; reduce or eliminate the growth of biological infectious agents downstream from the drain 24; and reduce contamination levels of surfaces exterior to the sink 10. For example, various embodiments of the present technology use one or more of germicidal ultra-violet lights, ozone water, copper-silver ionization solution, and a sanitizing agent to kill bacteria, parasites, fungi, viruses, molds and other biological contaminants that may grow within or be introduced into the open cavity 36.

In some embodiments, one or more germicidal ultra-violet lights 42 are associated with the sink 10. The light of the germicidal ultra-violet lights 42 is typically classified into three ranges of wavelength as follows: a) UV-A from 315 nanometers (nm) to 400 nm; b) UV-B from 280 nm to 315 nm; and c) UV-C from 100 nm to 280 nm. Embodiments of the sink 10 include one or more germicidal ultra-violet lights 42 within the open cavity 36. The germicidal ultra-violet lights 42 may be associated with 120 voltage power or low voltage power simply coupled with an adjacent power source, such as an outlet. Particular embodiments, of the present technology, use germicidal ultra-violet lights 42 in the 100 nm to 280 nm range and, in specific embodiments, a wavelength of 254 nm. Testing has indicated that, in an exemplary embodiment, a single, 17 inch long, ¾ inch diameter germicidal ultra-violet light 42 in these wavelength ranges will be sufficient to reduce biological contaminants within the open cavity 36. In the exemplary, non-limiting, embodiment depicted in FIG. 1A, the open cavity 36 is approximately 5.5 inches deep, 9 inches tall, and 18 inches wide. The germicidal ultra-violet lights 42 are positioned such that any fluids passing through the open cavity 36 or sit within the drain trap 38 are exposed to the ultraviolet light. The UV light exposure kills bacteria, parasites, fungi, viruses, molds and other biological contaminants that may be growing on the surfaces within the open cavity 36 and in the fluids within the drain trap 38. The UV light exposure also kills the contaminants that may be entrained within sewer and vent gases that occasionally travel back up through the drainage system opposite of the direction of the waste water flow and back "up" through the drain trap 38.

These gases have the potential to carry with them bacteria, parasites, fungi, viruses, molds and other biological contaminants that often deposit themselves on adjacent surfaces next to the plumbing fixture from which they are expelled such as surfaces of sinks, faucets, floors, walls, towels, clothing, or plumbing fixtures, etc.

In particular embodiments, elongated germicidal ultra-violet lights 42 are positioned within an upper area of the open cavity 36, adjacent a top portion of the sink 10, so that their lengths extend along a width of the open cavity 36 between the opposite side portions 20 and 22. In this location, the germicidal ultra-violet lights 42 are able to direct their light throughout the entire open cavity and into the drain trap 38 while staying substantially out of contact with any liquid flowing through the open cavity 36. In various embodiments, an interior of the open cavity 36, adjacent the drain 24, will be sloped concentrically or eccentrically to reduce fluid from splashing onto the germicidal ultra-violet lights 42. It is contemplated, however, that embodiments of the sink 10 will use a UV light assembly capable of withstanding damp/wet environments or being fully submerged in water. A fluid overflow may be incorporated in the design of the basin 12 in lieu of water-proofing the UV light enclosure. In various embodiments, lamp shields 46 are installed to separate the germicidal ultra-violet light 42 from an exhaust air passage between the exhaust port 40 and the drain 24 where liquids typically flow. The lamp shields 46 may also be designed to encompass the germicidal ultra-violet light 42. In some embodiments, the lamp shields 46 may be made from quartz or other type of transparent material that will not reduce the effectiveness of the germicidal ultra-violet lights 42. A high water sensor may also be incorporated in the design of the open cavity 36 in lieu of water-proofing the UV light enclosure. In embodiments, such as the exemplary embodiment depicted in FIG. 1B, the overflow orifice 17 penetrates the forward wall portion 16 below a level of the germicidal ultra-violet light 42 to prevent a clog or backflow from putting fluid in contact with the germicidal ultra-violet lights 42. In various embodiments of the present technology, the germicidal ultra-violet lights 42 remain on in order to continuously treat the open cavity 36 and a portion of the drain trap 38.

Embodiments of the present technology use one or more sanitizing agent injectors 44 and/or spray bars 45 at various locations throughout the open cavity 36 and/or into the exhaust port 40 to help clean the surfaces of the open cavity 36 and the exhaust port 40. Exemplary embodiments, depicted in FIGS. 1A-4, show a sanitizing agent injector 44 associated with the exhaust port 40. However, other locations throughout the open cavity 36 may include one or more sanitizing agent injectors 44. Similarly, with reference to FIGS. 3A-3D, one or more spray bars 45 can be positioned within the open cavity 36. As depicted, the spray bar 45 may be generally horizontally disposed along a width or depth of the open cavity 36. However, the spray bar 45 may also be vertically disposed. It is contemplated that the spray bar may provide one or more spray outlets along a length of the spray bar 45. The one or more sanitizing agent injectors 44 and spray bars 45 may inject one or more of: ozone water (or other ozone solution); copper-silver ionization solution (such as domestic cold water treated with a copper/silver ionization generation unit); or a sanitizing agent. The sanitizing agent injectors 44 and/or spray bars 45 are positioned throughout the open cavity 36 and exhaust port 40 in locations that will maximize distribution of the ozone water, copper-silver ionization solution, and/or a sanitizing agent throughout the open cavity 36. Testing has proven that the ozone water effectively reduces or eliminates the biological contaminants within the open cavity 36. The ozone water and/or sanitizing agent may be injected into the open cavity 36 continuously or intermittently, whether the sink 10 is in use, or not, depending on desired protocols or detected contaminant levels. An ozone water generator or ozone gas generator that creates higher or lower concentrations of ozone water solution may be associated with the sink 10. In a particular embodiment, the ozone water generator produces ozonized water with a concentration of 1.0-1.5 parts/million for injection within the sink 10. Similarly, a copper/silver ionization generator that creates different concentrations of copper/silver ions in water may be associated with the sink 10.

In various embodiments of the present technology, control systems provide monitoring and control to ensure that the features of the sink 10 are functioning according to their intended design. Such monitoring and control may prove beneficial in view of the fact that incorporated features, such as the exhaust port 40, germicidal ultra-violet lights 42, sanitizing agent injectors 44, and spray bar 45 play individual and, at times, combined roles in protecting the sink 10 and creating a contamination barrier between the sink 10 and its operational environment. In one aspect of the control systems, sensors are positioned within the open cavity 36 and/or the exhaust port 40 that monitor pressure and/or airflow. In such embodiments, the control system receives and monitors data from the sensors. The control system may be associated with the exhaust port 40 and its related systems to initiate, terminate, and vary the exhaust through the exhaust port 40 according to its comparison of the data received from the sensors with desired operational parameters. In another aspect of the control systems, sensors are positioned within the open cavity 36 and/or the drain trap 38 that monitor UV light and/or an amount of ozone water (or other ozone solution), copper-silver ionization solution, or similar sanitizing agent. In particular embodiments, the control systems will control the injection of the ozone water (or other ozone solution), copper-silver ionization solution, or similar sanitizing agent. This control system may direct the injection to occur on a timed interval, at any time that the faucet 30 is turned on or off, or according to data from the sensors that are not in line with desired or predetermined operational parameters.

Monitoring of the system ensures that all system safety components are properly functioning and will alert someone or something if service or maintenance is needed. The data received from the sensors may be recorded by the control system and reported to a user in real-time or stored for delivery or retrieval at a later time. In some embodiments, the control system status will be relayed through visual and/or audible indicators. Such indicators may be provided through a control panel and/or individual indicator lights or audible signals. On one example, a visual indicator may be provided by a green LED light visible when approaching the sink 10. Green, in this example, would mean the sink 10 is operational; while a red LED light indication may be provided to indicate the sink 10 may not be functioning to design specification and needs service or maintenance. Some embodiments of the control system will be placed in communication with a building automation system (BAS) or Internet of Things (TOT) cloud network for remote monitoring and control. Accordingly, the control system may be configured to store data and desired operational parameters and programs locally or remotely. The control system may be provided to receive remote or locally provided inputs from a user that initiates, terminates, and varies the operation of exhaust port 40, germicidal ultra-violet lights 42, sanitizing agent injectors 44, and spray bar 45. The control system may also receive remote or locally provided inputs from a user that varies the operational parameters or programs of the systems associated with the sink 10. The control system may be provided to provide a notification either locally (audible or visual) or electronically via e-mail, phone, or text message to initiate service and notify individuals to not use the sink 10 when the control system determines that any of the exhaust port 40, germicidal ultra-violet lights 42, sanitizing agent injectors 44, and spray bar 45 are not functioning properly. The control system may also be provided to monitor when any of the germicidal ultra-violet lights 42 is burned out and send a notification to initiate service and not use the sink 10. The control system can also be provided to monitor the germicidal ultra-violet lights 42 for annual maintenance or replacement.

Figure 4:
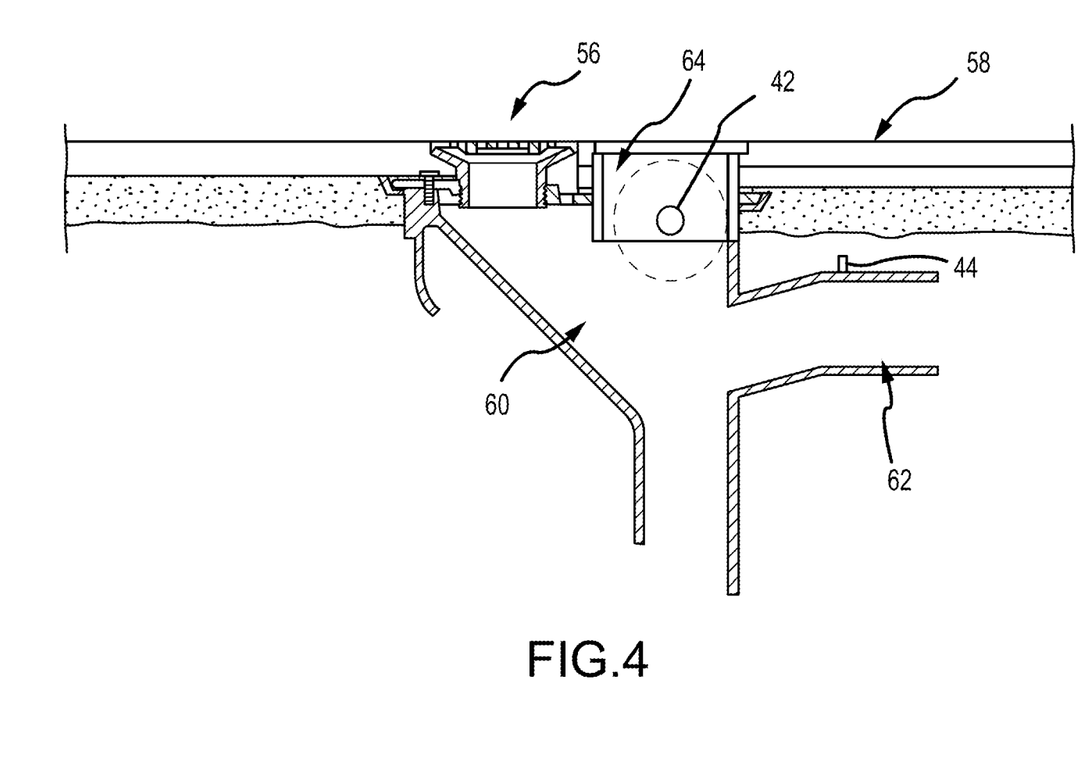
FIG. 4 depicts a cutaway, side elevation view of a floor drain according to the present technology.

With reference to FIG. 4, the present technology is easily applied to floor drains of various configurations and uses. In the exemplary, non-limiting embodiment depicted in FIG. 4, the floor drain 56 is positioned within a floor surface 58. An open cavity 60 is in fluid communication with, and extends beneath, the floor drain 56. An exhaust port 62 is in fluid communication with the open cavity 60. The exhaust port 62 will operate similarly, and in similar parameters, to the exhaust port 40 described above. The exhaust port 62 is placed in fluid communication with a central exhaust system or a dedicated exhaust system of various known designs (not depicted) that place the open cavity 60 under a negative pressure to evacuate the gaseous headspace of the open cavity 60 away from the floor drain 56. In various embodiments, a constant volume or variable speed fan may be associated with the exhaust port 62. In some embodiments, the gaseous exhaust may be directed to a system for treating one or more types of contaminated or volatile gases. In various embodiments, a germicidal ultra-violet light 42 is designed to be fuller submersible or installed in a waterproof floor box 64 and will operate similarly, and in similar parameters, to the germicidal ultra-violet light 42 described above. Embodiments of the floor drain 56 may also use one or more sanitizing agent injectors 44 and/or spray bars 45 (not depicted) at various locations throughout the open cavity 60 and/or into the exhaust port 62 to help clean the surfaces of the open cavity 60 and the exhaust port 62. The one or more sanitizing agent injectors 44 may inject one or more of: ozone water (or other ozone solution); copper-silver ionization solution (such as domestic cold water treated with a copper/silver ionization generation unit); or similar sanitizing agent and will operate similarly, and in similar parameters, to the sanitizing agent injectors 44 described above. It is further contemplated that one or more control systems, such as those described above may be associated with the floor drain 56 to provide monitoring and control functions.

Although the technology been described in language that is specific to certain structures, materials, and methodological steps, it is to be understood that the invention defined in the appended claims is not necessarily limited to the specific structures, materials, and/or steps described. Rather, the specific aspects and steps are described as forms of implementing the claimed invention. Since many embodiments of the invention can be practiced without departing from the spirit and scope of the invention, the invention resides in the claims hereinafter appended. Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Moreover, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

What is claimed is:

1. A system for treating and disposing of fluid, the system comprising:
   a basin defined by a bottom portion and at least one basin sidewall that extends upwardly from the bottom portion; the basin including a basin drain, adjacent the bottom portion, through which a fluid may exit the basin, and a drain trap in fluid communication with the basin drain;
   an open cavity separated from the basin by the at least one basin sidewall; the open cavity being in open fluid communication with the basin drain and aligned over the drain trap; and
   an exhaust port in open fluid communication with the open cavity, the basin drain, and an exhaust system that selectively places a positive draft on the exhaust port and places the open cavity under a negative pressure and exhausts away from the basin.

2. The system of claim 1 further comprising:
   a faucet positioned adjacent the basin and having a faucet outlet positioned above the basin; the faucet being in open fluid communication with a fluid source and adapted for the selective flow of fluid from the fluid source and out the faucet outlet.

3. The system of claim 2 wherein:
   a portion of the at least one sidewall in the basin including a lower transition portion having a concave radius positioned beneath the faucet outlet so that fluid flow from the faucet is received by the radius.

4. The system of claim 3 wherein:
   the lower transition portion includes a vertical portion that extends upwardly from the radius at a slight slope, toward a front portion of the sink.

5. The system of claim 4 wherein:
   the radius of the lower transition portion transitions into a lower sloped portion that passes beneath the basin drain.

6. The system of claim 5 wherein:
   a free, terminal end of the lower sloped portion defines an air gap that is positioned above a bottom portion of the open cavity.

7. The system of claim 6 further comprising:
   an air channel extends between the lower transition portion and a forward wall portion of the bottom portion of the open cavity and fluidly couples the open cavity with an environment exterior to the basin.

8. The system of claim 1 wherein:
   the basin drain penetrates a portion of the at least one basin sidewall above the bottom portion basin.

9. The system of claim 8 wherein:
   the basin drain includes a plurality of vertically spaced-apart bar members that are shaped to reduce fluid turbulence by allowing an even distribution of fluid to flow through the basin drain.

10. The system of claim 1 further comprising:
    a sanitizing agent injector, placed in open fluid communication with the open cavity.

11. The system of claim 10 wherein:
    the sanitizing agent injector is in fluid communication with a source of at least one of: an ozone solution; or a copper-silver ionization solution.

12. The system of claim 1 wherein:
    the exhaust system creates an airflow range of between 20 cubic feet per minute and 50 cubic feet per minute when no liquids are being passed through the basin drain.

13. The system of claim 1 wherein:
    the exhaust system creates an airflow range of between 50 cubic feet per minute and 500 cubic feet per minute when liquids are being passed through the basin drain.

14. The system of claim 1, further comprising:
    a germicidal ultra-violet light produces light in the 100 nm to 280 nm range.

15. The system of claim 1 further comprising:
    a lamp shield positioned within the open cavity to separate a germicidal ultra-violet light from an exhaust air passage between the exhaust port and the basin drain.

16. A method of treating and disposing of fluid, the method comprising:
    disposing a liquid into a basin, defined by a bottom portion and at least one basin sidewall that extends upwardly from the bottom portion, so that the liquid passes through a basin drain, into an open cavity separated from the basin by the at least one basin sidewall, and into a drain trap positioned adjacent a bottom portion of the open cavity; and
    placing a positive draft on an exhaust port with an exhaust system such that the open cavity is placed under negative pressure and a headspace of the open cavity is drawn through the exhaust port.

17. The method of claim 16 further comprising:
    injecting at least one of an ozone solution or a copper-silver ionization solution from a sanitizing agent injector within the open cavity.

18. The method of claim 16 further comprising:
    ceasing the of disposing liquid into the basin;
    reducing the positive draft on the exhaust port so that the exhaust system creates an airflow range of between 20 cubic feet per minute and 50 cubic feet per minute through the exhaust port and the open cavity.

19. The method of claim 16 further comprising:
    increasing the positive draft on the exhaust port so that the exhaust system creates an airflow range of between 50 cubic feet per minute and 500 cubic feet per minute through the exhaust port and the open cavity when liquids are being passed through the basin drain.

* * * * *